United States Patent
Dalko

US008461206B2

(10) Patent No.: US 8,461,206 B2
(45) Date of Patent: Jun. 11, 2013

(54) USE OF AT LEAST ONE (DIHYDRO)JASMONIC ACID DERIVATIVE FOR TREATING DRY SKIN

(75) Inventor: Maria Dalko, Gif S/Yvette (FR)

(73) Assignee: L'Oreal, Paris (FR)

( * ) Notice: Subject to any disclaimer, the term of this patent is extended or adjusted under 35 U.S.C. 154(b) by 171 days.

(21) Appl. No.: 12/407,359

(22) Filed: Mar. 19, 2009

(65) Prior Publication Data

US 2011/0085999 A9    Apr. 14, 2011

Related U.S. Application Data

(63) Continuation of application No. 10/768,132, filed on Feb. 2, 2004, now abandoned.

(60) Provisional application No. 60/452,108, filed on Mar. 6, 2003.

(30) Foreign Application Priority Data

Jan. 31, 2003  (FR) ..................................... 03 01146

(51) Int. Cl.
   *A01N 37/08*   (2006.01)
   *A01N 53/00*   (2006.01)
   *A61K 31/557*  (2006.01)

(52) U.S. Cl.
   CPC .................................. *A61K 31/557* (2013.01)
   USPC ........................................ 514/573; 514/530

(58) Field of Classification Search
   None
   See application file for complete search history.

(56) References Cited

U.S. PATENT DOCUMENTS

| | | | |
|---|---|---|---|
| 4,496,556 A | | 1/1985 | Orentreich |
| 5,861,532 A | | 1/1999 | Brown et al. |
| 6,019,992 A | * | 2/2000 | Carson et al. .................. 424/401 |
| 6,054,137 A | * | 4/2000 | Breton et al. .................. 424/400 |
| 6,086,903 A | | 7/2000 | Trinh et al. |
| 2003/0224024 A1 | | 12/2003 | Leveque et al. |

FOREIGN PATENT DOCUMENTS

| | | |
|---|---|---|
| EP | 1 031 554 A1 | 8/2000 |
| EP | 1 333 021 | 8/2003 |
| EP | 1 333 022 | 9/2003 |
| JP | 10-29935 | 2/1998 |
| JP | 10-59829 | 3/1998 |
| JP | 11-79948 | 3/1999 |
| JP | 2001-199832 * | 7/2001 |
| WO | WO 01/05388 | 1/2001 |
| WO | WO 01/05388 A2 | 1/2001 |

OTHER PUBLICATIONS

Ohta et al., Maturitas, 1998, vol. 30, pp. 55-62.*
Stewart, M.E., *Sebaceous Gland Lipids*, Seminars in Dermatology, vol. 11, No, 2, Jun. 1992: pp. 100-105.
Bhattacharyya, S.; Neidigh, K., Avery, M., Williamson, *Selective Monoalkylation of Ammonia: A High Throughput Synthesis of Primary Amines*, J., Synlett 1999, No. 11, pp. 1781-1783.
Cava, M. P., Vogt, B. R., *The Synthesis of A-Bisnorsteriods*, Tetrahedron Letters, No. 39, (1964), pp. 2813-2816.
Spreitzer, H., Buchbauer, G. and Püringer, Ch., *A Study of Selective Oxime Reduction Methods*, Tetrahedron vol. 45, No. 22, (1989), pp. 6999-7002.
Mayer, S.C., Joullié , M.M., *Incorporation of an Amino Function in A (1S, 2S, 3R) -3-Hydroxy-2-Methyl-1-Cyclohexahe Carbolic Acid*, Synthetic Communications, 24(16) (1994), pp. 2351-2365.
Adger, B.M., Farrell, C.O., Lewis, N. J., Mitchell, M.B., *Catalytic Transfer Hydrogenolysis of N-Benzyl Protecting Groups*, Communications, (1987), pp. 53-55.
Brown, E.G., Nuss, J. M., *Alkylation of Rink's Amide Linker on Polystyrene Resin: A Reductive Amination Approach to Modified Amine-Linkers for the Solid Phase Synthesis of N-Substituted Amide Derivations*, Tetrahedron Letters, vol. 38, No. 49, (1997), pp. 8457-8460.
Macor J.E., Ryan, K., *Synthesis of Some Conformationally Restricted Analogs of Serotonin*, Heterocycles, vol. 8, Aug. 1990, pp. 1497-1504.
Kozikowski, A.P., Schmiesing, *Synthesis of an Alleged Constituent of New Brunswick Cranberry Leaves: The So-Called Cannivonine*, J. Org. Chem. (1983), 48, pp. 1000-1007.
Whitlock, B.J., Whitlock, H.W., *Regiospecific Synthesis of Islandicin Methyl Ether*, J. Org. Chem. (1980), 45, pp. 12-15.
Kiyota, H., Higashi, E., Koike, T., Oritani, T., *Lipase-catalyzed preparation of both enantiomers of methyl jasmonate*, Tetrahedron: Asymmetry, 12 (2001), pp. 1035-1038.
Zouboulis, C. C., Seltmann, H., Neitzel, H., Orfanos, C.E., *Establishment and Characterization of an Immortalized Human Sebaceous Gland Cell Line (SZ95)*[1], The Society for Investigative Dermatology, Inc., (1999), pp. 1011-1020.
Database Beilstein [online], Beilstein Institute for Organic Chemistry, Frankfurt-Main, De, XP002282164, 2006.
Database Beilstein [online] Beilstein Institute for Organic Chemistry, Frankfurt-Main, DE, XP002282165, 2006.
Database Beilstein [online] Beilstein Institute for Organic Chemistry, Frankfurt-Main, DE, XP002282166, 2006.
Database Beilstein [online] Beilstein Institute for Organic Chemistry, Frankfurt-Main, DE, XP002282167, 2006.
Database Beilstein [online] Beilstein Institute for Organic Chemistry, Frankfurt-Main, DE, XP002282168, 2006.
Database Beilstein [online] Beilstein Institute for Organic Chemistry, Frankfurt-Main, DE, XP002282169, 2006.

(Continued)

*Primary Examiner* — Brian Gulledge
(74) *Attorney, Agent, or Firm* — Novak Druce Connolly Bove + Quigg LLP

(57) ABSTRACT

A cosmetic process for treating dry skin and/or a dry scalp of non-inflammatory origin, for example, in a menopausal woman, comprising topically applying to the skin and/or the scalp a composition comprising, in a physiologically acceptable medium, at least one (dihydro)jasmonic acid derivative; novel (dihydro)jasmonic acid derivatives and to the compositions, for example, suitable for topical application to the skin, comprising them.

16 Claims, No Drawings

OTHER PUBLICATIONS

Database Beilstein [online] Beilstein Institute for Organic Chemistry, Frankfurt-Main, DE, XP002282170, 2006.
Database Beilstein [online] Beilstein Institute for Organic Chemistry, Frankfurt-Main, DE, XP002282171, 2006.
Database Beilstein [online] Beilstein Institute for Organic Chemistry, Frankfurt-Main, DE, XP002282172, 2006.
Database Beilstein [online] Beilstein Institute for Organic Chemistry, Frankfurt-Main, DE, XP002282173, 2006.
Database Beilstein [online] Beilstein Institute for Organic Chemistry, Frankfurt-Main, DE, XP002282174, 2006.
Database Beilstein [online] Beilstein Institute for Organic Chemistry, Frankfurt-Main, DE, XP002282175, 2006.
Database Beilstein [online] Beilstein Institute for Organic Chemistry, Frankfurt-Main, DE, XP002282176, 2006.
Database Beilstein [online] Beilstein Institute for Organic Chemistry, Frankfurt-Main, DE, XP002282177, 2006.
Database Beilstein [online] Beilstein Institute for Organic Chemistry, Frankfurt-Main, DE, XP002282178, 2006.
Database Beilstein [online] Beilstein Institute for Organic Chemistry, Frankfurt-Main, DE, XP002282179, 2006.
English Language Derwent Abstract of JP 2001-199832.
English Language Derwent Abstract of 11-79948, 1999.
English Language Derwent Abstract of 10-59829, 1998.
English Language Derwent Abstract of 10-29235, 1998.
European Search Report for EP 1 442 737 A3, dated Aug. 4, 2004.
Database WPI, Section Ch, Week 199819, Derwent Publications Ltd., London, GB; Class B05, AN 1998-212696, XP002257101.
Patent Abstracts of Japan, vol. 2000, No. 24, May 11, 2001 & JP 2001 199832.
Patent Abstracts of Japan, vol. 1999, No. 08, Jun. 30, 1999 & JP 11 079948.
Database WPI, Section Ch, Week 199815, Derwent Publications Ltd., London, GB; Class B05, AN 1998-163664, XP002257102.
Hiroaki Ohta (1998) Relationship between dermato-physiological changes and hormonal status in pre-, peri- and postmenopausal women. Maturitis vol. 30, pp. 55-62.

* cited by examiner

USE OF AT LEAST ONE (DIHYDRO)JASMONIC ACID DERIVATIVE FOR TREATING DRY SKIN

This application is a continuation of application Ser. No. 10/768,132, filed Feb. 2, 2004 now abandoned, which claims the benefit of priority of French Patent Application No. 03 01146, filed Jan. 31, 2003, and claims priority to U.S. Provisional Application No. 60/452,108, filed Mar. 6, 2003, all of which are incorporated herein by reference.

Disclosed herein is a cosmetic process for treating dry skin and/or a dry scalp of non-inflammatory origin, for example, in a menopausal woman, comprising topically applying to the skin and/or the scalp at least one composition comprising, in a physiologically acceptable medium, at least one (dihydro) jasmonic acid derivative. Further disclosed herein are novel (dihydro)jasmonic acid derivatives and compositions comprising them, for example, compositions suitable for topical application to the skin.

Many women thirty-five years or older, for example, after menopause, frequently complain of the dryness of their skin, and of unaesthetic or uncomfortable manifestations resulting therefrom, such as desquamation, pale complexion, cutaneous atony. Now, as is now known, this dryness may be caused, among other things, by a decrease in the production of sebum with age.

Sebum is the natural product of the sebaceous gland, which, together with the sweat produced by the eccrine or apocrine glands, constitutes a natural moisturizer for the epidermis. Sebum consists essentially of a more or less complex mixture of lipids. Conventionally, the sebaceous gland produces squalene, triglycerides, aliphatic waxes, cholesterol waxes and possibly free cholesterol (Stewart, M. E., *Semin. Dermatol*, 11, 100-105 (1992)). The action of bacterial lipases converts a variable portion, and sometimes all, of the triglycerides into free fatty acids.

Sebocytes are the competent cells of the sebaceous gland. The production of sebum is associated with the program of terminal differentiation of these cells. During this differentiation, the metabolic activity of the sebocytes is essentially focused on the biosynthesis of lipids (lipogenesis), and more precisely on the neosynthesis of fatty acids and squalene.

A compound for stimulating the production of the lipids that form sebum, by the cells of the sebaceous gland (the sebocytes), could therefore be a definite advantage for the treatment of oligoseborrhoeic dry skin, a characteristic of menopausal women, i.e. skin with a sebum content of less than 100 μg/cm$^2$ on the forehead halfway through the day.

To this end, it has been proposed in U.S. Pat. No. 4,496,556 to use DHEA, a steroid secreted by the adrenal glands, or the esters thereof, administered topically, to increase the production of sebum.

However, for a certain number of legal and toxicological reasons, it may not always be possible to use compounds of this type in the cosmetic field. In addition, its efficacy may be insufficient on oligoseborrhoeic skin. There is thus still a need for cosmetically acceptable compounds allowing the sebaceous function to be efficiently stimulated, for the purpose of treating oligoseborrhoeic dry skin.

The present inventor has now discovered, surprisingly, that certain (dihydro)jasmonic acid derivatives may make it possible to satisfy this need.

It is known practice to use (dihydro)jasmonic acid derivatives which are analogues of prostaglandins as anti-inflammatory agents, for the purpose of treating problems with secretions, for example, salivary and lacrymal secretions, but also dry skin of inflammatory origin (WO 01/05388). It is also known practice, from Japanese Patent Application No. 2001-199 832, to use methyl dihydrojasmonate as a desquamating agent by activation of the proteases of the cornified layer, for example, in the treatment of dry skin. Finally, hair tonics are known which comprise jasmonic acid derivatives and which may, for example, be capable of retaining moisture in the scalp when they are incorporated into the lipid bilayer of a vesicle such as a liposome (JP-10 059 829).

However, it has not yet been suggested that (dihydro)jasmonic acid derivatives may be useful in treating dry skin and dry scalp, for example in menopausal women, which may be due to an insufficient secretion of sebum of hormonal origin which cannot be treated with anti-inflammatory agents and/or with desquamating agents.

To the contrary, Japanese Patent Application Nos. 11 079 948 and 10 029 235 disclose the anti-androgenic effect (demonstrated on mouse cancer cells) of compositions comprising dihydrojasmonic acid derivatives and possibly botanic extracts, and suggest using these compositions in the treatment of seborrhoea, which is essentially androgen-dependent.

Now, the present inventor has demonstrated at least one positive effect of (dihydro)jasmonic acid derivatives on the production of sebum.

Disclosed herein is thus a cosmetic process for treating dry skin and/or a dry scalp of non-inflammatory origin, for example, in a menopausal woman, comprising topically applying to the skin and/or the scalp a composition comprising, in a physiologically acceptable medium, at least one (dihydro)jasmonic acid derivative chosen from compounds of formula (I) and the isomers, stereoisomers and salts thereof:

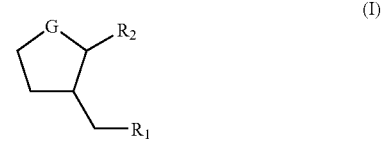

(I)

wherein:
G is a group chosen from: C=O; CH—ORa; CH—NRR'; C=CRbRc; CH—CHRbRc;

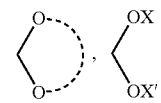

and CYY', wherein:
Ra is chosen from
hydrogen;
saturated and unsaturated, linear, branched and cyclic, C$_1$-C$_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from hydrogen, an aryl radical and saturated and unsaturated, linear and branched hydrocarbon-based radicals comprising from 1 to 4 carbon atoms; and
radical —CO-Rd, wherein Rd is chosen from saturated and unsaturated, linear and branched alkyl, aryl, aralkyl and alkoxy groups comprising from 1 to 17 carbon atoms, optionally substituted with at least one group chosen from hydroxyl and methoxy groups;

Rb and Rc, which may be identical or different, are each chosen from groups R and groups —COORe, wherein Re is chosen from $C_1$-$C_4$ hydrocarbon-based radicals;

R and R', which may be identical or different, are each chosen from hydrogen, saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R"', —NHCOR", halogen, —CN, —COOR" and —OR", wherein R" and R"', which may be identical or different, are each chosen from hydrogen, an aryl radical and saturated and unsaturated, linear and branched hydrocarbon-based radicals comprising from 1 to 4 carbon atoms, or R and R' may form at least one ring with the atom to which they are attached;

the dots of formula

represent a saturated or unsaturated, divalent hydrocarbon-based radical comprising from 1 to 3 carbon atoms, optionally substituted with at least one radical chosen from $C_1$-$C_6$ alkyl radicals and an aryl radical;

X and X', which may be identical or different, are each chosen from saturated and unsaturated hydrocarbon-based radicals comprising from 1 to 3 carbon atoms;

Y and Y', which may be identical or different, are each chosen from halogens;

$R_1$ is a radical chosen from —COOR, —CONRR', —CH$_2$OR, —COR, —CH$_2$R', —SO$_2$OR, —PO$_3$RR', —NHR and —NRR', wherein R and R' have the meanings indicated above; and $R_2$ is chosen from saturated and unsaturated, linear, branched and cyclic, $C_1$-$C_{18}$ hydrocarbon-based radicals optionally substituted with 1 to 5 identical or different entities chosen from —OR", —OCOR", —SR", —SCOR", NR"R"', —NHCOR", halogen, —CN, —COOR" and —COR", wherein R" and R"' have the meaning indicated above.

The compounds of formula (I) wherein G is CH—NRR' may be prepared according to the following reaction scheme:

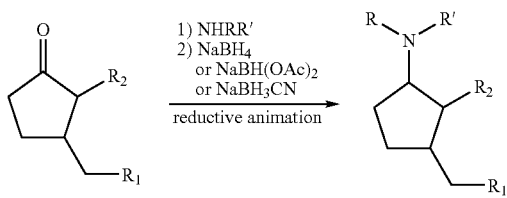

according to a process described, for example, in S. Bhattacharyya, *Synlett*, 1999, 11, 1781-1783; S. Bhattacharyya, M. P. Cava, *Tetrahedron Lett.*, 1964, 2813; H. Speitzer, *Tetrahedron*, 1989, 45, 22, 6999; S. C. Mayer, *Synthetic Comm.*, 1994, 24, 16, 2351-2365; B. M. Adger, *Synthesis*. 1987, 53; E. G. Brown, *Tetrahedron Lett.*, 1997, 38, 49, 8457-8460; U.S. Pat. No. 5,861,532; J. E. Macor, *Heterocycles*, 1990, 31, 8, 1497-1504; and A. P. Kozikowski, *J. Org. Chem.*, 1983, 48, 1000.

The compounds of formula (I) wherein G is C=CRbRc may be prepared according to the following reaction scheme:

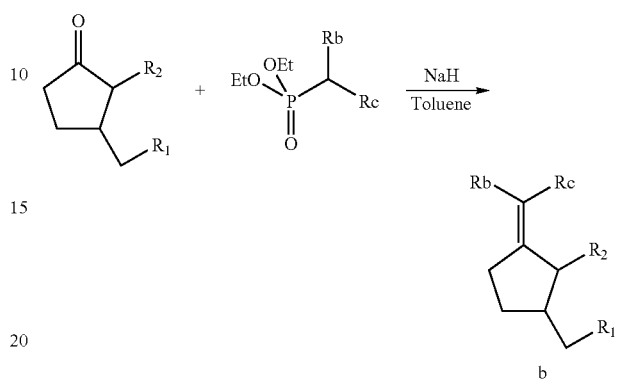

by a Wittig reaction in toluene in the presence of sodium hydride as base.

The compounds of formula (I) wherein G is CH—CHRbRc may be prepared from the above compounds, by forming a reduction of their double bond by means of catalytic hydrogenation in the presence of palladium-on-charcoal (10%), of triethanolamine and of formic acid, followed by saponification of the diester thus obtained and isolated.

The compounds of formula (I) wherein G is

may be prepared according to the following reaction scheme:

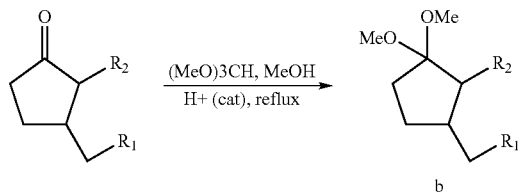

It is a conventional reaction for protection of the carbonyl group.

The compounds of formula (I) wherein G is CYY', wherein Y and Y' are each a fluorine atom may be synthesized as described in *Journal of Organic Chemistry*, 45, 14 (1980), by reaction corresponding dihydrojasmonate with Et$_2$NSF$_3$ (DAST).

The other compounds of formula (I) may be prepared according to a process similar to those given in the examples below.

Further disclosed herein is the cosmetic use of at least one (dihydro)jasmonic acid derivative as defined herein, as an agent for treating dry skin and/or dry scalp of non-inflammatory origin, for example, in menopausal women.

Even further disclosed herein, is a cosmetic process for treating dry skin and/or a dry scalp of non-inflammatory origin, comprising topically applying to the skin and/or the scalp a composition comprising, in a physiologically acceptable medium, at least one (dihydro)jasmonic acid derivative chosen from compounds of formula (I) and the isomers, stereoisomers and salts thereof:

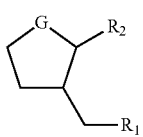
(I)

wherein:

G is a group chosen from: CH—ORa; CH—NRR'; C=CRbRc; CH—CHRbRc;

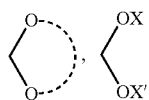

and CYY', wherein:

Ra is chosen from
saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from a hydrogen atom, an aryl radical and a saturated and unsaturated, linear and branched hydrocarbon-based radical comprising from 1 to 4 carbon atoms; and
radical —CO-Rd wherein Rd is chosen from saturated and unsaturated, linear and branched alkyl, aryl, aralkyl and alkoxy groups comprising from 1 to 17 carbon atoms, optionally substituted with at least one group chosen from hydroxyl and methoxy groups;

Rb and Rc, which may be identical or different, are each chosen from groups R and groups —COORe, wherein Re is chosen from $C_1$-$C_4$ hydrocarbon-based radicals;

R and R', which may be identical or different, are each chosen from hydrogen, saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from a hydrogen atom, an aryl radical and a saturated and unsaturated, linear and branched hydrocarbon-based radical comprising from 1 to 4 carbon atoms, or R and R' form at least one ring with the atom to which they are attached;

the dots of formula

represent a saturated or unsaturated, divalent hydrocarbon-based radical comprising from 1 to 3 carbon atoms, optionally substituted with at least one radical chosen from a $C_1$-$C_6$ alkyl radical and an aryl radical;

X and X', which may be identical or different, are each chosen from saturated and unsaturated hydrocarbon-based radicals comprising from 1 to 3 carbon atoms;

Y and Y', which may be identical or different, are each chosen from halogens;

$R_1$ is a radical chosen from —COOR, —CONRR', —CH$_2$OR, —COR, —CH$_2$R', —SO$_2$OR, —PO$_3$RR', —NHR and —NRR', wherein R and R' have the meanings indicated above; and $R_2$ is chosen from saturated and unsaturated, linear, branched and cyclic, $C_1$-$C_{18}$ hydrocarbon-based radicals optionally substituted with 1 to 5 identical or different entities chosen from —OR", —OCOR", —SR", —SCOR", NR"R'", —NHCOR", halogen, —CN, —COOR" and —COR", wherein R" and R'" have the meaning indicated above.

Also disclosed herein is a cosmetic process for treating dry skin and/or a dry scalp of non-inflammatory origin, comprising topically applying to the skin and/or the scalp a composition comprising, in a physiologically acceptable medium, at least one (dihydro)jasmonic acid derivative chosen from compounds of formula (I) and the isomers, stereoisomers and salts thereof:

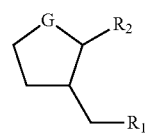
(I)

wherein:

G is a group C=O;

$R_1$ is a radical chosen from —COOR, —CONRR', —CH$_2$OR, —COR, —CH$_2$R', —SO$_2$OR, —PO$_3$RR', —NHR and —NRR', wherein R and R', which may be identical or different, are each chosen from hydrogen, saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from a hydrogen atom, an aryl radical and a saturated and unsaturated, linear and branched hydrocarbon-based radical comprising from 1 to 4 carbon atoms, or R and R' form at least one ring with the atom to which they are attached; and $R_2$ is chosen from saturated, linear, branched and cyclic, $C_1$-$C_{18}$ hydrocarbon-based radicals optionally substituted with 1 to 5 identical or different entities chosen from —OR", —OCOR", —SR", —SCOR", NR"R'", —NHCOR", halogen, —CN, —COOR" and —COR", wherein R" and R'" have the meaning indicated above.

Even further disclosed herein are (dihydro)jasmonic acid derivatives chosen from compounds of formula (II) and the isomers, stereoisomers and salts thereof:

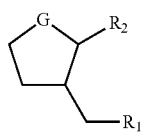

(II)

wherein:
G is a group chosen from CH—ORa; CH—NRR'; C=CRbRc; and CH—CHRbRc, wherein:
Ra is chosen from saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from hydrogen, an aryl radical and saturated and unsaturated, linear and branched hydrocarbon-based radicals comprising from 1 to 4 carbon atoms; and
R, R', Rb and Rc, which may be identical or different, are each chosen from hydrogen and saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from hydrogen, an aryl radical, and saturated and unsaturated, linear and branched hydrocarbon-based radicals comprising from 1 to 4 carbon atoms, or R and R' (or respectively, Rb and Rc) may form at least one ring with the atom to which they are attached;
$R_1$ is a radical chosen from —COOR, —CONRR', —CH$_2$OR, —COR, —CH$_2$R', —SO$_2$OR, —PO$_3$RR', —NHR and —NRR', wherein R and R' have the meaning indicated above;
$R_2$ is chosen from saturated and unsaturated, linear, branched and cyclic, $C_1$-$C_{18}$ hydrocarbon-based radicals optionally substituted with 1 to 5 identical or different entities chosen from —OR", —OCOR", —SR", —SCOR", NR"R'", —NHCOR", halogen, —CN, —COOR" and —COR", wherein R" and R'" have the meaning indicated above,
with the proviso that G is not —CH—NH—(CH$_2$)$_2$—N(CH$_3$)$_2$ when $R_2$ is a n-pentyl radical and $R_1$ is radical —COOR.

The compounds of formula (II) may be prepared by the methods disclosed, for example, above, and other compounds of formula (II) may be prepared according to a process similar to those given in the examples below.

In one embodiment, $R_1$ may be radical —COOR, wherein R has the definition indicated above and, for example, may be chosen from hydrogen and unsubstituted, saturated and unsaturated, linear, branched and cyclic, $C_1$-$C_6$ hydrocarbon-based radicals; and/or $R_2$ may be chosen from unsubstituted, saturated and unsaturated, linear and branched hydrocarbon-based radicals comprising from 1 to 10 carbon atoms, for example, an n-pentyl radical.

Examples of such compounds include those wherein: G is CH—N(CH$_3$)$_2$; $R_1$ is chosen from radicals —COOH and —COOCH$_3$; and $R_2$ is a n-pentyl radical.

Even further disclosed herein are novel (dihydro)jasmonic acid derivatives chosen from compounds of formula (III) and the isomers, stereoisomers and salts thereof:

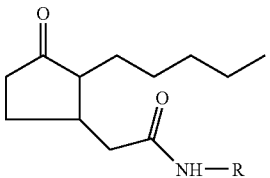

(III)

wherein:
R is chosen from hydrogen and saturated and unsaturated, linear, branched and cyclic, $C_1$-$C_{12}$ hydrocarbon-based radicals optionally substituted with one to five identical or different entities chosen from —OR", —OCOR", —SR", —SCOR", NR"R'", —NHCOR", halogen, —CN, —COOR" and —COR", wherein R" and R'", which may be identical or different, are each chosen from hydrogen, an aryl radical and saturated and unsaturated, linear and branched hydrocarbon-based radicals comprising from 1 to 4 carbon atoms.

The compounds of formula (III) may be prepared by activation of the dihydrojasmonic acid with carbonyl diimidazole in anhydrous THF at ambient temperature, and then addition, at ambient temperature, of a primary amine R—NH$_2$ in solution in THF.

Further embodiments disclosed herein are directed to a composition, for example, suitable for topical application to the skin and/or the scalp, comprising, in a physiologically acceptable medium, at least one (dihydro)jasmonic acid derivative chosen from compounds of formulae (I), (II), and (III) as defined above.

Even further embodiments disclosed herein are directed to a cosmetic process for skincare, for cleansing the skin and/or for making up the skin, comprising topically applying to the skin a composition comprising, in a physiologically acceptable medium, at least one (dihydro)jasmonic acid derivative chosen from compounds of formulae (I), (II), and (III) as defined above, and a cosmetic process for conditioning and/or for cleansing the hair, comprising topically applying to the hair a composition comprising, in a physiologically acceptable medium, at least one (dihydro)jasmonic acid derivative chosen from compounds of formulae (I), (II), and (III) as defined above.

The compositions disclosed herein may, for example, be intended to be applied to individuals exhibiting insufficient sebum secretion, such as menopausal women, who generally have a sebum content of less than 100 μg/cm$^2$ on the forehead, characteristic of an oligoseborrhoeic skin and/or scalp.

The compositions disclosed herein may make it possible to restore the production of sebum by the sebocytes and, may also, improve the comfort of dry skin and dry scalp. It may also make it possible to combat the dull and/or lifeless appearance of the skin and/or of the hair resulting from them drying out.

The compounds of formula (I), and certain embodiments of formula (II), which may, for example, be used in the compositions disclosed herein are those wherein G is a group chosen from C=O and CH—ORa, wherein Ra is chosen from hydrogen and unsubstituted, saturated and unsaturated, linear and branched hydrocarbon-based radicals comprising from 1 to 12 carbon atoms; $R_1$ is a radical —COOR, wherein R has the definition indicated above; and $R_2$ is chosen from unsubstituted, saturated and unsaturated, linear and branched hydrocarbon-based radicals comprising from 1 to 10 carbon atoms.

For example, G is a group chosen from C=O and CH—OH; $R_1$ is a radical —COOR, wherein R is chosen from hydrogen and unsubstituted, saturated and unsaturated, linear and branched hydrocarbon-based radicals comprising from 1 to 6 carbon atoms, for example, a methyl radical; and $R_2$ is chosen from unsubstituted, saturated and unsaturated, linear and branched hydrocarbon-based radicals comprising 5 carbon atoms, for example, a n-pentyl radical.

An example of such a compound is methyl dihydrojasmonate (or one of the isomers, stereoisomers and salts thereof), which is, for example, commercially available from the company FIRMENICH under the commercial reference HEDIONE 964898.

Other compounds which can be used in the compositions disclosed herein include, for example, methyl jasmonate which can be prepared as described in KIYOTA et al., "Lipase-Catalyzed Preparation of Both Enantiomers of Methyl Jasmonate," *Tetrahedron: Assymetry*, Vol. 12, No. 7, pages 1035-1038 (2001); and the compounds wherein: G is a group —CH—OH, for example, the compounds wherein $R_1$=COOCH$_3$ and $R_2$ is chosen from a n-pentyl radical and a 2,3-pentenyl radical.

Further examples of compounds of formulae (I) and (II) include those wherein G is a group CH—ORa, wherein Ra is chosen from linear and branched $C_1$-$C_6$ hydrocarbon-based radicals substituted with at least one group chosen from —OH, —COOH and —NH$_2$; $R_1$ is a radical —COOR, wherein R has the definition indicated above; and $R_2$ is chosen from unsubstituted, saturated and unsaturated, linear and branched hydrocarbon-based radicals comprising from 1 to 10 carbon atoms.

Even further examples of such compounds include those wherein: G is a group chosen from CH—OCH$_3$, CH—O—CH$_2$—COOH, CH—O—CH$_2$—CH$_2$—NH$_2$, and CH—O—CH$_2$—CH(OH)—CH$_2$OH; $R_1$ is a radical —COOR, wherein R is chosen from hydrogen and unsubstituted, saturated and unsaturated, linear and branched hydrocarbon-based radicals comprising from 1 to 6 carbon atoms; and $R_2$ is a n-pentyl radical.

Other examples of compounds of formulae (I) and (II) which can be used are those wherein: G is a group CH—ORa, wherein Ra is a radical —CO—Rd, wherein Rd is chosen from saturated and unsaturated, linear and branched alkyl, aryl, aralkyl and alkoxy groups comprising from 1 to 17 carbon atoms, optionally substituted with at least one group chosen from hydroxyl and methoxy groups; $R_1$ is a radical —COOR; and $R_2$ is chosen from unsubstituted, saturated and unsaturated, linear and branched hydrocarbon-based radicals comprising from 1 to 10 carbon atoms.

Examples of such compounds include those wherein: G is a group chosen from CH—O—CO—CH$_2$CH$_3$ and CH—O—CO—(C$_6$H$_4$OH); $R_1$ is a radical —COOR, wherein R is chosen from hydrogen and unsubstituted, saturated and unsaturated, linear and branched hydrocarbon-based radicals comprising from 1 to 6 carbon atoms; and $R_2$ is a n-pentyl radical.

Further examples of compounds of formula (I) include compounds wherein: G is a group C=O; $R_1$ is a radical —CO—NH—R; and $R_2$ is chosen from unsubstituted, saturated and unsaturated, linear and branched hydrocarbon-based radicals comprising 5 carbon atoms, for example, a n-pentyl radical.

Even further examples of compounds which can be used in the disclosed compositions include those wherein, respectively: G is a group chosen from CF$_2$ and CH—N—(CH$_3$)$_2$, $R_1$ is a radical —COOR, wherein R is chosen from hydrogen and unsubstituted, saturated and unsaturated, linear and branched hydrocarbon-based radicals comprising from 1 to 6 carbon atoms; and $R_2$ is a n-pentyl radical.

The concentration of the at least one (dihydro)jasmonic acid derivative which can be used according to the present disclosure depends of course on the desired effect and can therefore vary to a large extent. In one embodiment, the at least one (dihydro)jasmonic acid derivative may be present in an amount ranging, for example, from 0.01% to 20% by weight, relative to the total weight of the composition, such as, for example, from 0.1% to 10% by weight, relative to the total weight of the composition, and from 0.5% to 5% by weight, relative to the total weight of the composition.

The compositions disclosed herein may, for example, be suitable for topical application to the skin and/or the scalp, and it therefore comprises a physiologically acceptable medium, i.e. a medium which is compatible with the skin, its appendages (eyelashes, nails, hair) and/or the mucous membranes.

The compositions disclosed herein may be provided in all pharmaceutical forms normally used in the cosmetics and dermatological fields, and it may, for example, be in a form chosen from optionally gelled solutions, lotion dispersions, optionally two-phase lotions, emulsions obtained by dispersion of a fatty phase in an aqueous phase (O/W) or conversely (W/O), and triple emulsions (W/O/W or O/W/O) and vesicular ionic and nonionic dispersions. These compositions may be prepared according to the methods known by those of ordinary skill in the art. In one embodiment, the composition disclosed herein may be in the form of an oil-in-water emulsion.

The compositions disclosed herein may, for example, be more or less fluid and may, for example, be provided in a form chosen from white or colored creams, ointments, milks, lotions, serums, pastes and mousses. It may optionally, for example, be applied in the form of an aerosol. It may, for example, also be in solid form, such as in the form of a stick. It may be used, for example, as a care product and/or as a makeup product for the skin. The compositions disclosed herein may also, for example, be provided in a form chosen from shampoos and conditioners.

In a known manner, the compositions disclosed herein used may further comprise at least one adjuvant that is common in the cosmetics field. For example, the at least one adjuvant may be chosen from hydrophilic and lipophilic gelling agents, hydrophilic and lipophilic active agents, preserving agents, antioxidants, solvents, fragrances, fillers, screening agents, pigments, odor absorbers and dyestuffs. The amount of the at least one adjuvant is that conventionally used in the field under consideration and, for example, may range from 0.01 to 20% by weight, relative to the total weight of the composition. Depending on its nature, the at least one adjuvant may be introduced into the fatty phase, into the aqueous phase and/or into lipid vesicles. In any event, the at least one adjuvant, and also the proportions thereof, will be chosen so as not to harm the desired properties of the at least one (dihydro)jasmonic acid derivative disclosed herein.

When the compositions disclosed herein is provided in the form of a emulsion, the fatty phase may, for example, be present in an amount ranging from 5% to 80% by weight, such as, for example, from 5% to 50% by weight, relative to the total weight of the composition. The oils, the emulsifiers and the coemulsifiers used in the composition in the form of an emulsion are chosen from those conventionally used in the cosmetics field. The emulsifiers and the coemulsifiers may, for example, be present in the composition in a total amount ranging from 0.3 to 30% by weight, such as, for example, from 0.5 to 20% by weight, relative to the total weight of the composition.

The oils which may be used in the compositions disclosed herein may, for example, be chosen from mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax or ozokerite) may also be used as fatty substances.

For example, the oils and the other fatty substances may comprise those naturally present in sebum, such as squalene, triglycerides and cholesterol waxes.

The emulsifiers and coemulsifiers may, for example, be chosen from fatty acid esters of polyethylene glycol, such as PEG-100 stearate, and fatty acid esters of glycerol, such as glyceryl stearate.

The hydrophilic gelling agents may, for example, be chosen from carboxyvinyl polymers (carbomer), acrylic copolymers such as acrylate/alkyl acrylate copolymers, polyacrylamides, polysaccharides, natural gums and clays, and lipophilic gelling agents, for example, modified clays such as bentones, dextrin palmitate and hydrophobic silica.

In certain embodiments the compositions disclosed herein may comprise at least one agent chosen from desquamating agents; moisturizers; anti-inflammatory agents and calmatives; agents for stimulating keratinocyte proliferation and/or differentiation; anti-hairloss agents; antidandruff agents; and antibacterial agents.

In fact, stimulation of seborrhoea by the at least one (dihydro)jasmonic acid derivative disclosed herein may, in some individuals, provide an area of proliferation for the resident microflora of the follicular ostium (*Propionibacterium acnes*, for example), thus causing considerable hydrolysis of the sebum triglycerides to free fatty acids and reduction of the unsaturations of the polyunsaturated fatty acids (linoleic acid, for example). These two phenomena may contribute to keratinization of the infundibulum and to the formation of a microcomedone. This may degenerate into a comedone, plugging and dilating the pore in an unaesthetic manner. At a more advanced stage, this plug may become an inflammatory acne lesion.

By adding desquamating agents and/or agents for stimulating keratinocyte proliferation or differentiation to the compositions disclosed herein, it may be possible to avoid the formation of these comedones. Similarly, antibacterial and/or bacteriostatic agents may also make it possible to obtain the same effect, by moderating proliferation of the resident microflora.

In additional embodiments, moisturizers may complete the effect obtained when using the disclosed at least one (dihydro)jasmonic acid derivative, and calmatives may, for example, improve the comfort of oligoseborrhoeic dry skin.

In further embodiments, the use of anti-hairloss and/or antidandruff agents may be used when the compositions disclosed herein is intended for the treatment of a dry scalp.

Various embodiments disclosed herein will now be illustrated by the following nonlimiting examples. In these examples, the amounts are indicated as percentage by weight.

EXAMPLES

Example 1

Process for Preparing Alcohol Derivatives of (Dihydro)Jasmonic Acid

The process below may be used, by analogy, to synthesize other jasmonic acid derivatives of formula (I) wherein G=CH—OH.

Step 1: Synthesis of (+/−)-jasmonic Acid or (+/−)-(1R,2R)-3-oxo-2-[(2Z)-2-pentenyl]cyclopentaneacetic Acid

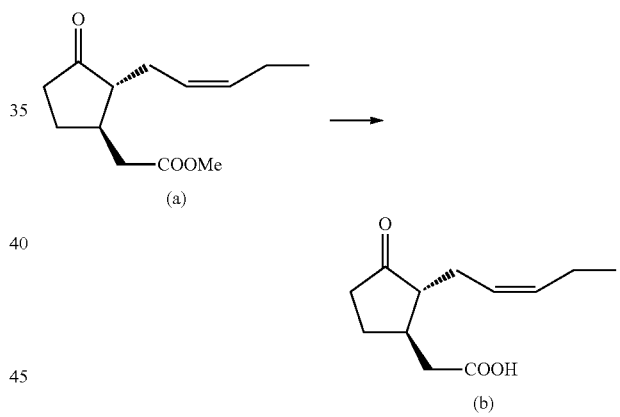

In a 250 ml three-necked flask equipped with a refrigerant, a thermometer and a magnetic stirring device, 15 g (66.9 mmol) of (+/−)-methyl jasmonate (a) was dissolved in 150 ml of acetone. 10 ml of aqueous sodium hydroxide solution (5.35 g, 133.7 mmol) was added slowly. The mixture was stirred for 5 hours at ambient temperature. The acetone was then evaporated off under vacuum and the residual aqueous phase was then washed with ethyl acetate (2×30 ml). The aqueous phase was acidified to pH=2 with hydrochloric acid, and was then extracted with dichloromethane (3×30 ml).

The organic phase was dried over sodium sulphate, filtered through filter paper, and then concentrated. The light brown oil obtained was dried under vacuum.

13.6 g of (+/−)-jasmonic acid (b) were obtained, i.e. a yield of 97%. The $^1$H NMR spectrum and the mass spectrum (negative ionization) were in accordance with the expected structure.

Step 2: Synthesis of (+/−)-(1R,2R)-3-hydroxy-2-[(2Z)-2-Pentenyl]cyclopentaneacetic Acid

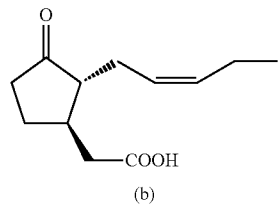

(b)

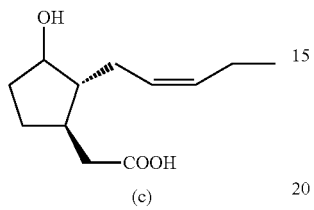

(c)

In a 50 ml three-necked flask equipped with a refrigerant, a thermometer and a magnetic stirring device, 1 g (4.8 mmol) of (+/−)-jasmonic acid (b) was dissolved in 15 ml of absolute ethanol. 430 mg (11.4 mmol) of sodium borohydride NaBH$_4$ was added. The mixture was stirred for 4 hours at 50° C. Once the reaction had ended, 5 ml of water was slowly added. The precipitate formed was filtered off. The filtrate was acidified to a pH=5 with hydrochloric acid and was then extracted with ethyl acetate (3×30 ml). The organic phase was dried over sodium sulphate, filtered through filter paper, and then concentrated. The colorless oil obtained was purified by silica gel chromatography (eluent: dichloromethane/methanol). The colorless oil obtained was dried under vacuum.

400 mg of the desired compound (c) was obtained, i.e. a yield of 40%. The $^1$H NMR spectrum was in accordance with the expected structure.

Example 2

Process for Preparing Ether Derivatives of (Dihydro)Jasmonic Acid

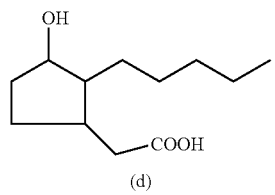

(d)

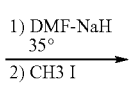

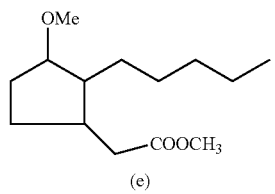

(e)

In a round-bottomed flask, 2.6 g of compound (d) was dissolved in 35 ml of dimethylformamide. 1.2 g of sodium hydride in suspension at 60% in oil was then added, the mixture was left to react for one hour at 35° C., and 1.8 ml of methyl iodide was then added. The mixture was left to react overnight at 35° C. After concentration of the reaction medium in a rotary evaporator, the residue was taken up with water and then extracted with dichloromethane. The organic phases was washed with water and then dried over sodium sulphate. After evaporation to dryness, 3 g of oil was obtained. This product was purified by column (silica gel) chromatography, the elution being carried out with a pentane/ethyl acetate mixture.

400 mg of pure product (e) was obtained (yield: 15%).

Example 3

Process for Preparing Alkyl Amides of (Dihydro)Jasmonic Acid

The process below may be used, by analogy, to prepare other compounds of formula (I) wherein R$_1$ is radical CO—NRR' and G is either a group C═O or a group —CH—OR.

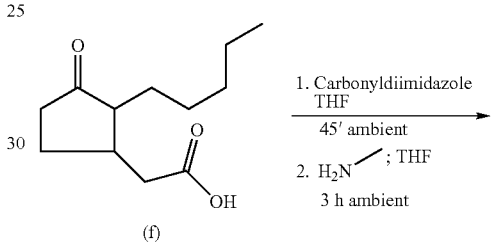

(f)

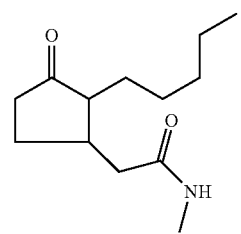

(g)

The dihydrojasmonic acid (f) was activated with 1.2 equivalents of carbonyldiimidazole in anhydrous THF at ambient temperature. It was determined that the reaction was complete after 45 minutes. One equivalent of methylamine in a 2M solution in THF was then added to the activated medium. The mixture was left to react for 3 hours at ambient temperature. The resulting product was treated and purified on a silica column. 300 mg of pure product (g) was recovered (yield: 50%). The mass spectrum and the NMR confirmed that the expected structure was obtained.

Example 4

Process for Preparing Alkyl Esters of (Dihydro)Jasmonic Acid

The process below may be used, by analogy, to prepare other compounds of formula (I) wherein R$_1$ is an alkoxycarbonyl radical and G is either a group C═O or a group —CH—OR.

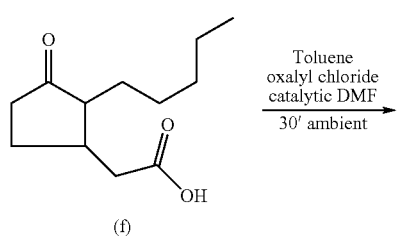

(f)

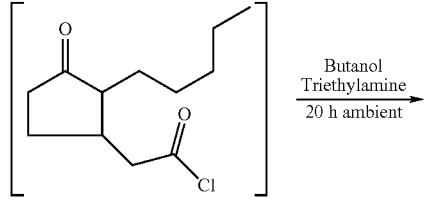

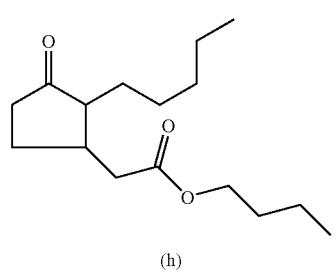

(h)

The dihydrojasmonic acid (f) was first activated with 2.1 equivalents of oxalyl chloride, in toluene, with DMF catalysis. It was determined that the reaction was complete after 30 minutes. The medium was then concentrated in a rotary evaporator. The acid chloride prepared above was solubilized in butanol in the presence of 2.1 equivalents of triethylamine. The mixture was left to react for 20 hours at ambient temperature, before treatment and purification on a silica column.

400 mg of product (h) was thus recovered (yield: 63%). The mass spectrum and the NMR confirm that the expected structure was obtained.

Example 5

Process for Preparing Acetal Derivatives of (Dihydro)Jasmonic Acid

The process below may be used, by analogy, to prepare other compounds of formula (I) wherein G comprises an acetal functional group.

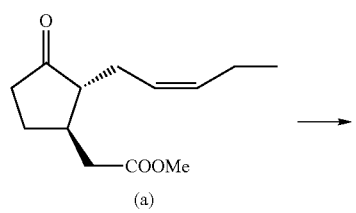

(a)

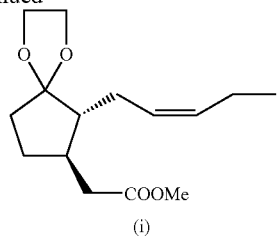

(i)

10 g of methyl jasmonate (44.6 mmol) (a) was dissolved in 100 ml of toluene in a 250 ml three-necked flask equipped with a Dean Stark apparatus, a thermometer and a magnetic stirring device. 20 g of ethylene glycol (322.2 mmol) and then 2.51 g of pyridinium tosylate (10 mmol) were added. The mixture was stirred at reflux for 16 hours, distilling the water formed by means of the Dean Stark apparatus. The reaction medium was then concentrated to dryness. The residue was taken up with 200 ml of methyl tert-butyl ether and then washed successively with an aqueous NaHCO$_3$ solution and with aqueous saline solution. The organic phase was dried over sodium sulphate, filtered through filter paper, and then concentrated.

11.5 g of oil was obtained, the oil was dried under vacuum (yield: 96%).

The $^1$H NMR spectrum of the compound (i) obtained was in conformity with the expected structure.

Example 6

Demonstration of the Activity of the (Dihydro)Jasmonic Acid Derivatives on Lipogenesis Methyl dihydrojasmonate (provided by BEDOUKIAN) was tested on a model of immortalized human sebocytes in culture, derived from the SZ95 line described in Zouboulis, C. C., Seltmann, H., Neitzel, H. & Orfanos, C. E., Establishment and Characterization of an Immortalized Human Sebaceous Gland Cell Line, *J. Invest. Dermatol.*, 113, 1011-1020 (1999).

The test consisted in measuring the amount of lipids produced by the sebocytes of the line (at confluence), in the presence or absence of active agent diluted in DMSO, such that the final amount of DMSO in the culture medium was 0.1% and the amount of methyl dihydrojasmonate was $10^{-4}$ M. After treatment for 48 hours, the adherent cells were treated with Nile Red (1 µg/ml). The lipid content was then quantified by measuring the fluorescence of the dye (two excitation/emission couples: 485-540 nm for the neutral lipids and 540-620 nm for the normeutral lipids). The results were given for the total lipids (combination of the two measurements).

The experiment was carried out in sextuplicate (assayed products and control) in a 96-well plate, and repeated four times.

For the samples treated with methyl dihydrojasmonate, the amount of neutral lipids synthesized by the sebocytes was increased by 98% compared to the untreated control ($p<0.001$).

This compound therefore induced a very significant increase in sebocyte lipogenesis.

Cell proliferation (MUH) and viability (LDH) assays made it possible to verify, in parallel, that the effects obtained were not related to a modification of these biological parameters.

Example 7

Cosmetic Composition

This composition is prepared in a manner which is conventional for those skilled in the art. The amounts are indicated as percentages by weight.

| | |
|---|---|
| Methyl dihydrojasmonate | 0.001% |
| 5-n-Octanoylsalicylic acid | 1% |
| Methylparaben | 0.1% |
| Propylparaben | 0.1% |
| Lanolin | 5% |
| Liquid petroleum jelly | 4% |
| Sesame oil | 4% |
| Cetyl alcohol | 5% |
| Glyceryl monostearate | 2% |
| Triethanolamine | 1% |
| Propylene glycol | 5% |
| Carbomer 940 | 0.1% |
| Water qs | 100% |

This cream, which is contemplated for use in twice daily applications, may make it possible to revive the radiance and improve the comfort of dry skin in menopausal women.

What is claimed is:

1. A cosmetic process for treating dry skin and/or a dry scalp of non-inflammatory origin in a menopausal woman by increasing the production of sebum, comprising topically applying a composition comprising, in a physiologically acceptable medium, at least one (dihydro)jasmonic acid derivative chosen from compounds of formula (1) and the stereoisomers and salts thereof:

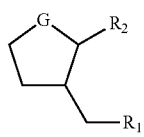

(I)

wherein:
G is a group chosen from: C=O and CH—OH
$R_1$ is a radical —COOR,
wherein R is chosen from hydrogen, saturated and unsaturated, linear, branched and cyclic, $C_1$-$C_{12}$ hydrocarbon-based radicals; and
$R_2$ is chosen from saturated and unsaturated, linear, branched and cyclic, $C_1$-$C_{18}$ hydrocarbon-based to the skin and/or the scalp of a menopausal woman in need thereof; and
wherein said at least one (dihydro)jasmonic acid derivative is present in an amount sufficient for increasing said production of sebum.

2. The process according to claim 1, wherein:
$R_2$ is chosen from unsubstituted, saturated and unsaturated, linear and branched hydrocarbon-based radicals comprising from I to 10 carbon atoms.

3. The process according to claim 2, wherein:
$R_1$ is a radical —COOR,
R is chosen from hydrogen and unsubstituted, saturated and unsaturated, linear and branched hydrocarbon-based radicals comprising from 1 to 6 carbon atoms; and
$R_2$ is chosen from unsubstituted, saturated and unsaturated, linear and branched hydrocarbon-based radicals comprising 5 carbon atoms.

4. The process according to claim 3, wherein:
$R_1$ is a radical —COOR, wherein R is a methyl radical; and
$R_2$ is an n-pentyl radical.

5. The process according to claim 1, wherein the
at least one (dihydro)jasmonic acid derivative is chosen from methyl dihydrojasmonate and the stereoisomers and salts thereof.

6. The process according to claim 1, wherein the at least one (dihydro)jasmonic acid derivative is present in an amount ranging from 0.01% to 20% by weight, relative to the total weight of the composition.

7. The process according to claim 6, wherein the at least one (dihydro)jasmonic acid derivative is present in an amount ranging from 0.1% to 10% by weight, relative to the total weight of the composition.

8. The process according to claim 7, wherein the at least one (dihydro)jasmonic acid derivative is present in an amount ranging from 0.5% to 5% by weight, relative to the total weight of the composition.

9. The process according to claim 1, wherein the composition further comprises at least one adjuvant chosen from hydrophilic and lipophilic gelling agents, hydrophilic and lipophilic active agents, preserving agents, antioxidants, solvents, fragrances, fillers, screening agents, pigments, odor absorbers and dyestuffs.

10. The process according to claim 1, wherein the composition further comprises at least one agent chosen from desquamating agents; moisturizers; anti-inflammatory agents and calmatives; agents for stimulating keratinocyte proliferation and/or differentiation; anti-hair-loss agents; antidandruff agents; and antibacterial agents.

11. The process according to claim 1, wherein the composition is in the form of an oil-in-water emulsion.

12. The process according to claim 11, wherein the fatty phase in the oil-in-water emulsion is present an amount ranging from 5% to 80% by weight, relative to the total weight of the composition.

13. The process according to claim 12, wherein the fatty phase in the oil-in-water emulsion is present in an amount ranging from 5% to 50% by weight, relative to the total weight of the composition.

14. The process according to claim 1, wherein the composition is applied to individuals having a sebum content of less than 100 µg/cm² on the forehead.

15. The process according to claim 1, wherein the process is effective for combating the dull and/or lifeless appearance of the skin and/or of the hair.

16. A cosmetic process for treating dry skin and/or a dry scalp of non-inflammatory origin in a menopausal woman by increasing the production of sebum, comprising topically applying a composition comprising, in a physiologically acceptable medium, at least one (dihydro)jasmonic acid derivative chosen from compounds of formula (1) and the stereoisomers and salts thereof:

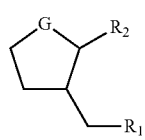

(I)

wherein:

G is a group C=O:

$R_1$ is a radical —COOR, wherein R is chosen from hydrogen, saturated and unsaturated, linear, branched and cyclic, $C_1$-$C_{12}$ hydrocarbon-based radicals; and $R_2$ is chosen from saturated and unsaturated, linear, branched and cyclic, $C_1$-$C_{18}$ hydrocarbon-based radicals to the skin and/or the scalp of a menopausal woman in need thereof; and wherein said at least one (dihydro)jasmonic acid derivative is present in an amount sufficient for increasing said production of sebum.

* * * * *